United States Patent [19]

Itoh et al.

[11] Patent Number: 5,013,623
[45] Date of Patent: May 7, 1991

[54] ELECTROPHOTOGRAPHIC PHOTORECEPTOR WITH STILBENE COMPOUND

[75] Inventors: Akira Itoh; Kozo Haino; Makoto Okaji; Kazuhiro Emoto; Tatsuya Kodera, all of Tsukuba, Japan

[73] Assignee: Mitsubishi Paper Mills Limited, Tokyo, Japan

[21] Appl. No.: 462,540

[22] Filed: Jan. 3, 1990

[30] Foreign Application Priority Data

Jan. 10, 1989 [JP] Japan ................................. 1-3967
Jan. 18, 1989 [JP] Japan ................................. 1-10329

[51] Int. Cl.$^5$ .................... G03G 5/06; G03G 5/047
[52] U.S. Cl. ...................................... 430/59; 430/73; 430/77; 430/78; 430/79
[58] Field of Search .................. 430/59, 73, 77, 78, 430/79

[56] References Cited

U.S. PATENT DOCUMENTS

| | | | |
|---|---|---|---|
| 3,246,983 | 4/1966 | Sus et al. ........................... | 430/73 X |
| 3,873,311 | 3/1975 | Contois et al. ...................... | 430/73 |
| 4,450,218 | 5/1984 | Takei et al. ......................... | 430/59 |
| 4,451,545 | 5/1984 | Hashimoto et al. .................. | 430/59 |
| 4,606,988 | 8/1986 | Sasaki ................................... | 430/59 |
| 4,622,278 | 11/1986 | Kondo et al. ........................ | 430/59 |
| 4,769,302 | 9/1988 | Ueda ................................... | 430/59 |
| 4,891,289 | 1/1990 | Ueda ................................... | 430/59 |
| 4,948,689 | 8/1990 | Kuroda et al. ....................... | 430/59 |

FOREIGN PATENT DOCUMENTS

| | | | |
|---|---|---|---|
| 0092255 | 10/1983 | European Pat. Off. .............. | 430/59 |
| 58-147747 | 9/1983 | Japan ................................... | 430/79 |
| 1-155358 | 6/1989 | Japan ................................... | 430/77 |

Primary Examiner—Roland Martin
Attorney, Agent, or Firm—Cushman, Darby & Cushman

[57] ABSTRACT

Disclosed is an electrophotographic photoreceptor which is high is sensitivity and high in endurance and which contains in photosensitive layer a novel stilbene compound represented by the following formulas [I], [II], or [III]:

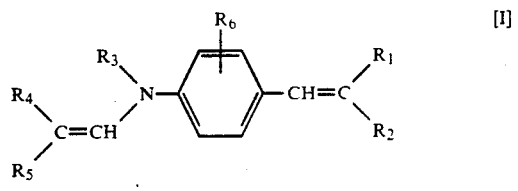

9 Claims, 2 Drawing Sheets

ELECTROPHOTOGRAPHIC PHOTORECEPTOR WITH STILBENE COMPOUND

BACKGROUND OF THE INVENTION

The present invention relates to an electrophotographic photoreceptor which contains a novel stilbene compound.

Hitherto, inorganic photoconductive substances such as selenium, cadmium sulfide, zinc oxide and silicon have been known for photoreceptors of electrophotographic system and widely studied and some of them have been put to practical use. Recently, organic photoconductive materials have also been intensively studied as electrophotographic photoreceptors and some of them have been practically used.

In general, inorganic materials are unsatisfactory, for example, selenium materials have problems such as deterioration in heat stability and characteristics due to crystallization and difficulty in production and cadmium sulfide materials have problems in moisture resistance, endurance and disposal of industrial waste. On the other hand, organic materials have advantages such as good film-formability, excellent flexibility, light weight, high transparency and easy designing of photoreceptors for wavelength of wide region by suitable sensitization. Thus, organic materials have increasingly attracted public attention.

Photoreceptors used in electrophotographic technique are required to possess the following fundamental properties, namely, (1) high chargeability for corona discharge in the dark place, (2) less leakage of the resulting charge in the dark place (dark decay), (3) rapid release of charge by irradiation with light (light decay), and (4) less residual charge after irradiation with light.

Extensive research has been made on photoconductive polymers as organic photoconductive substances including polyvinylcarbazole, but these are not necessarily sufficient in film-formability, flexibility and adhesion and besides these cannot be said to have sufficiently possess the above-mentioned fundamental properties as photoreceptor.

On the other hand, in case of organic low molecular photoconductive compounds, photoreceptors excellent in film-formability, adhesion, flexibility and other mechanical strength can be obtained therefrom by selection of binders and others used for formation of photoreceptors, but it is difficult to find compounds suitable to keep the characteristic of high sensitivity.

In order to improve these problems, there has been made development of organic photoreceptors having higher sensitivity by bearing the carrier generating function and the carrier transporting function by different substances. Characteristic of such photoreceptor called double-layered structure is that materials suitable for respective functions can be selected from wide variety of materials and photoreceptors having optional performances can be easily produced and thus intensive research has been made on such photoreceptors.

As explained above, many improvements have been made in production of electrophotographic photoreceptors, but those which meet the requirements for fundamental properties mentioned above and high endurance have not yet been obtained.

SUMMARY OF THE INVENTION

The object of the present invention is to provide an electrophotographic photoreceptor having high sensitivity and high endurance and especially to provide an electrophotographic photoreceptor which is high in charge characteristics, shows substantially no reduction of sensitivity after repeated use and is stable in charge potential.

DESCRIPTION OF THE INVENTION

Figure 1:
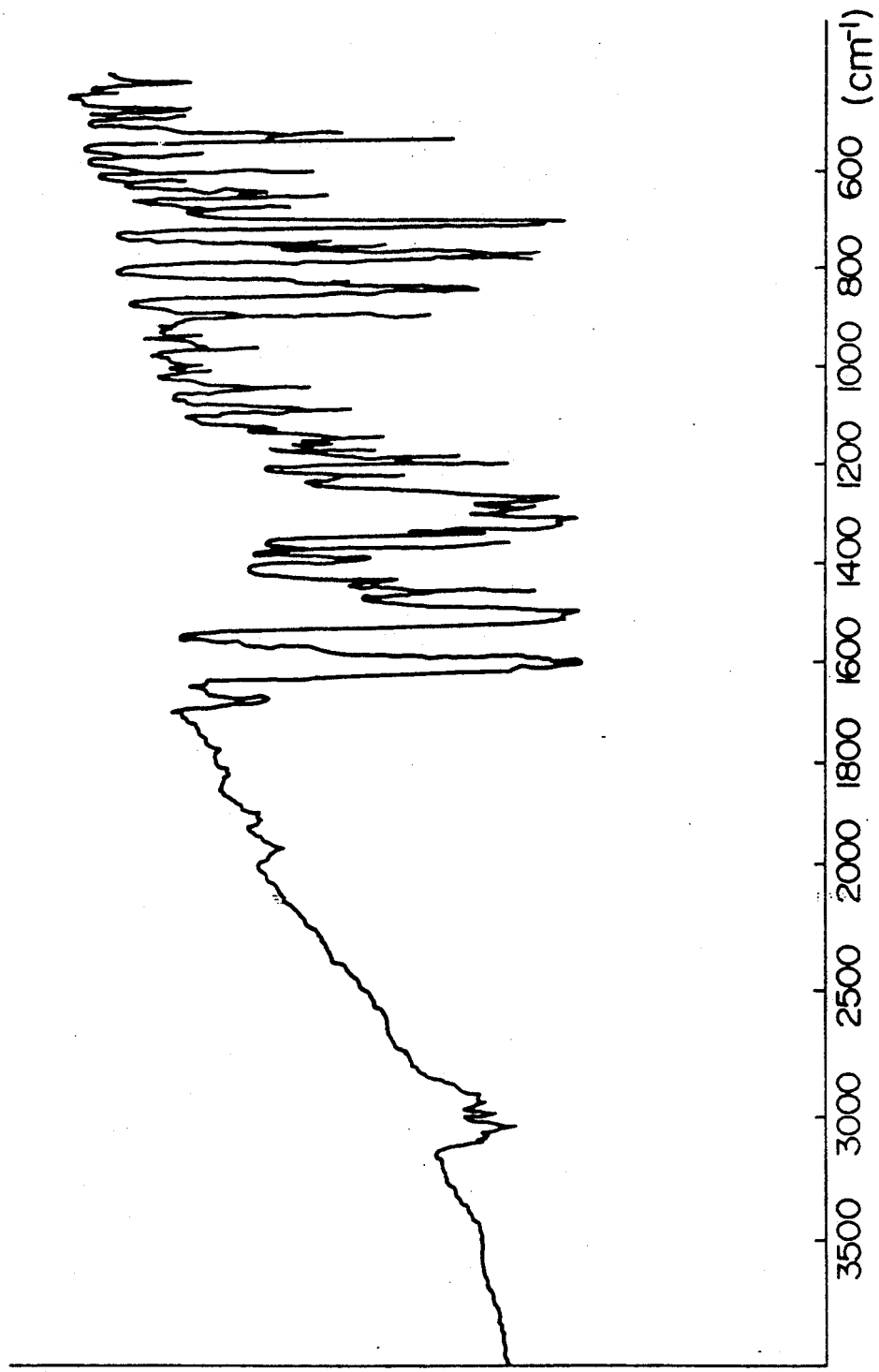
FIG. 1 shows infrared absorption spectrum of compound I-(1) exemplified hereinafter.

As a result of research conducted by the inventors on photoconductive substances having high sensitivity and high endurance, it has been found that the novel stilbene compounds represented by the formula [I], [II], and [III] are effective and the present invention has been accomplished.

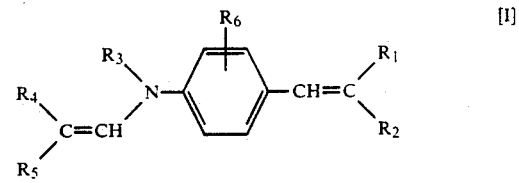

[I]

(wherein $R_1$ and $R_2$ which may be identical or different each represents a hydrogen atom or an alkyl, aryl or styryl group which may have substituent and at least one of them is an aryl or styryl group which may have substituent; $R_3$ represents an alkyl, aralkyl, or aryl group which may have substituent; $R_4$ and $R_5$ which may be identical or different each represents a hydrogen atom, or an alkyl, benzyl or phenyl group which may have substituent, and $R_6$ represents a hydrogen atom, or an alkyl or alkoxy group which may have substituent, or a halogen atom).

Examples of the substituents $R_1$ and $R_2$ are hydrogen atom; alkyl groups such as methyl group, ethyl group, n-propyl group, isopropyl group, and butyl group; aryl groups and substituted aryl groups such as phenyl group, naphthyl group, anthryl group, tolyl group, xylyl group, chlorophenyl group, methoxyphenyl group, bromophenyl group, ethoxyphenyl group, methylnaphthyl group, methoxynaphthyl group, and chloronaphthyl group; styryl group; substituted styryl groups such as p-chlorostyryl group, p-methoxystyryl group and p-methylstyryl group. Examples of substituent $R_3$ are alkyl groups such as methyl group, ethyl group, n-propyl group, isopropyl group, and butyl group; aralkyl and substituted aralkyl groups such as benzyl, phenylethyl group, naphthylmethyl group, methylbenzyl group, ethylbenzyl group, chlorobenzyl group, methoxybenzyl group and methoxyphenylethyl group; and aryl groups and substituted aryl groups such as phenyl group, naphthyl group, tolyl group, xylyl group, chlorophenyl group, methoxyphenyl group, and methylnaphthyl group. Examples of substituent $R_4$ and $R_5$ are hydrogen atom; alkyl groups such as methyl group, ethyl group, and propyl group; benzyl group; substituted benzyl groups such as chlorobenzyl group and methyl benzyl group; phenyl group; substituted phenyl groups such as methoxyphenyl group, tolyl group, and chlorophenyl group. Examples of substituent $R_6$ are hydrogen atom; alkyl groups such as methyl group and ethyl group; alkoxy groups such as methoxy group and ethoxy group; and halogen atoms such as chlorine and bromine.

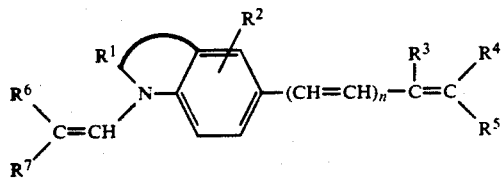

(wherein $R^1$ represents an atom group necessary to form a ring together with nitrogen atom; $R^2$ represents a hydrogen atom, or an alkyl or alkoxy group which may have substituent; $R^3$ represents a hydrogen atom, an alkyl or aryl group which may have substituent; $R^4$ represents an aryl group which may have substituent; $R^5$ represents a hydrogen atom, an alkyl, aralkyl group or aryl group which may have substituent; $R^6$ and $R^7$ which may be identical or different each represents a hydrogen atom, or an alkyl, aralkyl or aryl group which may have substituent and $R^6$ and $R^7$ may form a ring; and n represents 0 or 1).

Examples of rings formed by $R^1$ and nitrogen atom, etc. are carbazole ring, phenoxazine ring, phenothiazine ring and tetrahydroquinoline ring. Examples of substituent $R^2$ are hydrogen atom, alkyl groups such as methyl group, ethyl group, and propyl group; and alkoxy groups such as methoxy group, ethoxy group and propoxy group. Examples of the substituent $R^3$ are hydrogen atom; alkyl groups such as methyl group, ethyl group and propyl group; and aryl groups such as phenyl group, tolyl group, methoxyphenyl group, and chlorophenyl group. Examples of the substituent $R^4$ are aryl groups such as phenyl group, naphthyl group, ethoxyphenyl group, tolyl group, xylyl group and chlorophenyl group. Examples of $R^5$ are hydrogen atom; alkyl groups such as methyl group, ethyl group, propyl group and butyl group; aralkyl groups such as benzyl group, β-phenylethyl group, chlorobenzyl group, methylbenzyl group, methoxybenzyl group and α-naphthylmethyl group; and aryl groups such as phenyl group, naphthyl group, methoxyphenyl group, ethoxyphenyl group, tolyl group, xylyl group, and chlorophenyl group.

Examples of $R^6$ and $R^7$ are hydrogen atom; alkyl groups such as methyl group, ethyl group and propyl group; aralkyl groups such as benzyl group, methylbenzyl group, β-phenylethyl group, chlorobenzyl group, methylbenzyl group, methoxy benzyl group, α-naphthylmethyl group; and aryl groups such as phenyl group, naphthyl group, methoxyphenyl group, ethoxyphenyl group, tolyl group, xylyl group, and chlorophenyl group.

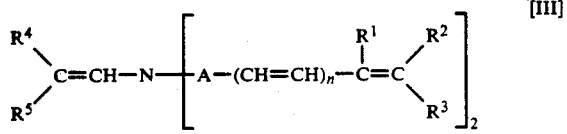

(wherein A represents an aromatic ring and the two A may link through a bond, an atom or an atom group to form a heterocyclic ring together with nitrogen atom; $R^1$ represents a hydrogen atom, or an alkyl or aryl group which may have substituent; $R^2$ represents an aryl group which may have substituent; $R^3$ represents an alkyl, aralkyl or aryl group which may have substituent; $R^4$ and $R^5$ which may be identical or different each represents a hydrogen atom, or an alkyl aralkyl or aryl group which may have substituent and $R^4$ and $R^5$ may form a ring; and n represents 0 or 1).

Examples of A are aromatic rings such as benzene ring and naphthalene ring and carbazole ring and phenothiazine ring as the nitrogen-containing heterocyclic rings formed by the above linkage.

Examples of substituent $R^1$ are hydrogen atom; alkyl groups such as methyl group, ethyl group and propyl group; and aryl groups such as phenyl group, tolyl group, methoxyphenyl group, and chlorophenyl group; Examples of $R^2$ are aryl groups such as phenyl group, naphthyl group, methoxyphenyl group, ethoxyphenyl group, tolyl group, xylyl group and chlorophenyl group.

Examples of $R^3$ are alkyl groups such as methyl group and ethyl group; aralkyl groups such as benzyl group and p-methylbenzyl group; and aryl groups such as phenyl group and p-methoxyphenyl group.

Examples of $R^4$ and $R^5$ are hydrogen atoms; alkyl groups such as methyl group, ethyl group, propyl group and butyl group; aralkyl groups such as benzyl group, β-phenylethyl group, chlorobenzyl group, methylbenzyl group, methoxybenzyl group, and α-naphthylmethyl group; and aryl groups such as phenyl group, naphthyl group, methoxyphenyl group, ethoxyphenyl group, tolyl group, xylyl group and chlorophenyl group.

The stilbene compounds represented by the formulas [I], [II] and [III] can be prepared by the processes as shown in the following synthesis examples.

SYNTHESIS EXAMPLE 1

Compound I-(1) exemplified hereinafter

Six grams of diethylbenzhydryl phosphonate and 5 g of N-β-methallyl-diphenylamine-4-carboxaldehyde were dissolved in 45 ml of DMF, followed by adding 3.4 g of potassium-t-butoxide under cooling with stirring. This was stirred at room temperature for 5 hours. The reaction mixture was poured into water and oily precipitate was extracted with benzene and the extracted oily matter was column chromatographed to obtain the desired product. This was a solid having yellow fluorescence. m.p. 85°–87° C. Yield: 2.0 g Structure of this compound was confirmed by NMR method. Infrared absorption spectrum of this compound is shown in FIG. 1.

SYNTHESIS EXAMPLE 2

Compound I-(8) exemplified hereinafter

Three grams of α-naphthylmethyl diethyl phosphonate and 2.5 g of N-β-metallyldiphenylamine-4-carboxaldehyde were dissolved in 20 ml of DMF, followed by adding 2.4 g of potassium-t-butoxide at room temperature with stirring. Reaction was allowed to proceed for 3 hours at room temperature and the reaction mixture was poured into water. The precipitated yellow solid was collected by filtration and recrystallized twice from acetonitrile. m.p. 96°–98° C. Yield: 3.0 g Its structure was confirmed by NMR method.

Figure 2:
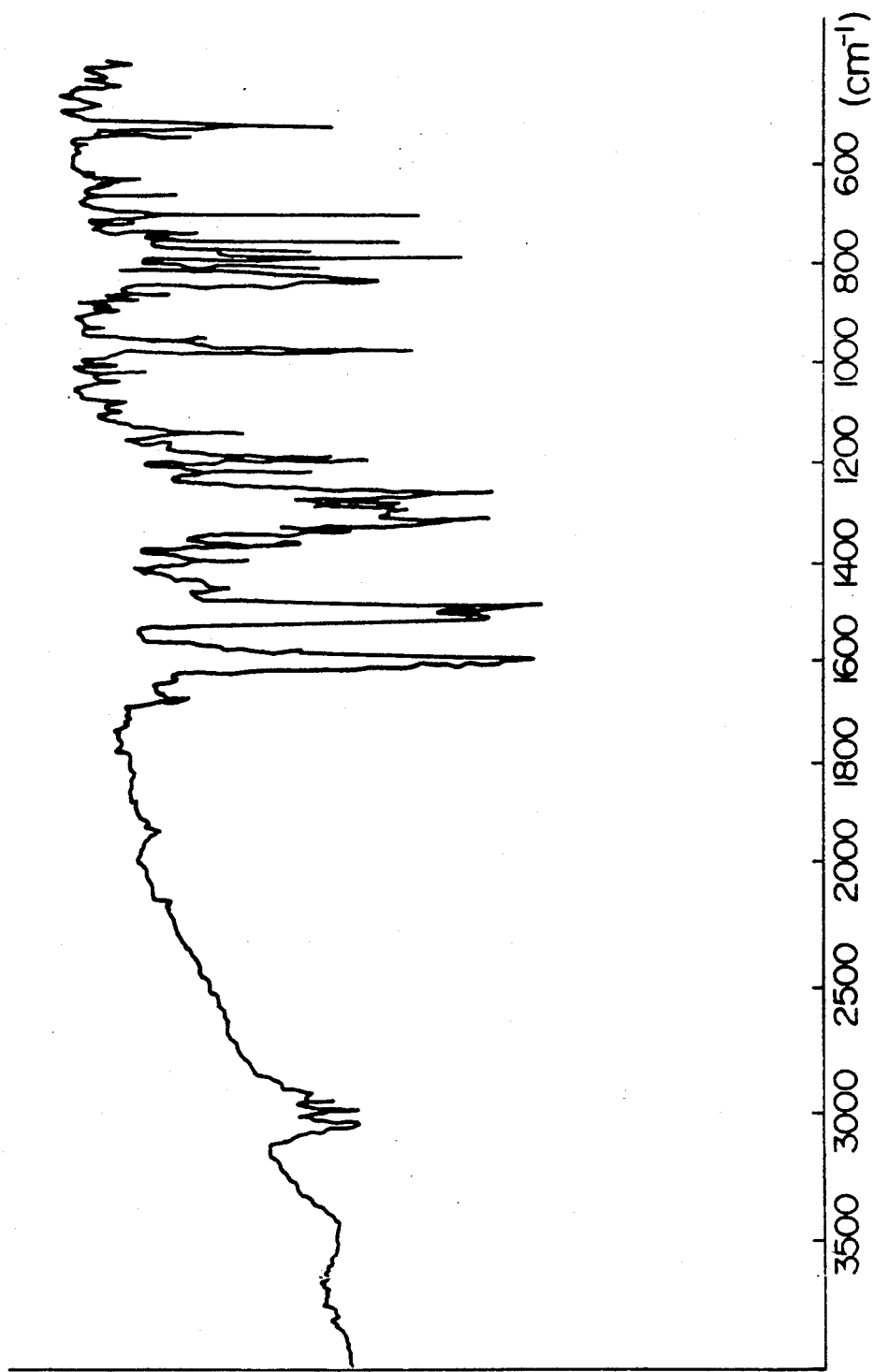
FIG. 2 shows infrared absorption spectrum of compound I-(8) exemplified hereinafter.

Infrared absorption spectrum of this compound is shown in FIG. 2.

As can be seen from the above synthesis examples, the process for synthesis of the stilbene compound of the present invention comprises carrying out the Wittig reaction using a kind of solvent in the presence of alkali. In this case, it has been found that the double bond of β-alkenylamino group is isomerized to form a stilbene compound having enamine structure. This structure is effective as photoconductor.

SYNTHESIS EXAMPLE 3

Compound II-(13)

2.49 Grams of aldehyde represented by the following formula [IV] and 3.34 g of phosphate ester represented by the formula [V] were dissolved in 15 ml of DMF and thereto was added 2.24 g of potassium-t-butoxide under cooling with water. After 3 hours at room temperature, the reaction mixture was poured into water and extracted with ethyl acetate. The crude product was purified by silica gel column (hexane: benzene=3:1) to obtain 3.70 g of compound II-(13).

NMR (δ, ppm, DMSO) 1.52(s, 3 H)
2.01(s, 3 H), 6.57(s, 1 H), 7.0–7.5
(m, 16 H), 7.74(s, 1 H), 7.79(d, J=7),
5 Hz, 1 H).

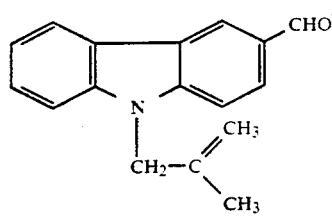
[IV]

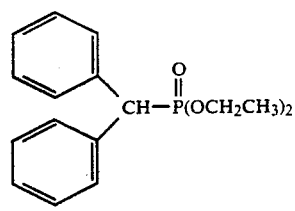
[V]

SYNTHESIS EXAMPLE 4

Compound III-(2)

2.32 Grams of stilbene compound represented by the formula (VI) was dissolved in 20 ml of DMSO and thereto was added 1.12 g of potassium-t-butoxide at room temperature. After 30 minutes, the reaction mixture was poured into water and extracted with benzene. The crude product was purified by alumina column (hexane: benzene=3:1) to obtain 2.01 g of compound II-(2).

NMR (δ, ppm, CDCl₃) 1.27(s, 3 H), 1.69
(s, 3 H), 5.75(s, 1 H), 6.7–6.9(m, 10 H),
7.2–7.4(m, 20 H)

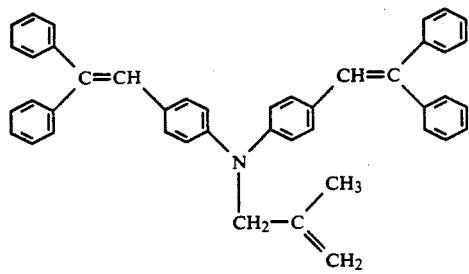
[VI]

Examples of the stilbene compounds represented by the formulas [I], [II] and [III] are shown below. The present invention is not limited to these examples.

Examples of the compounds represented by the formula [I]:

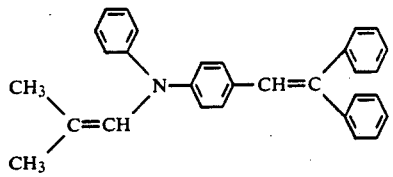
I-(1)

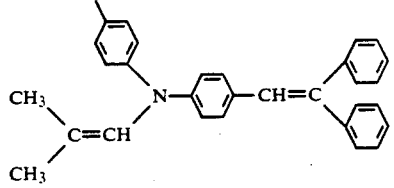
I-(2)

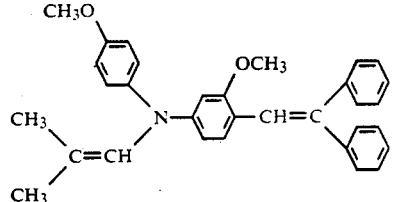
I-(3)

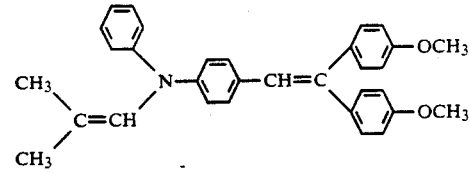
I-(4)

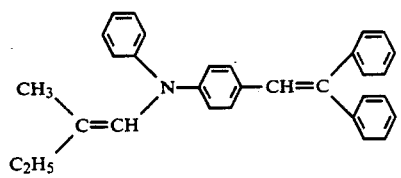
I-(5)

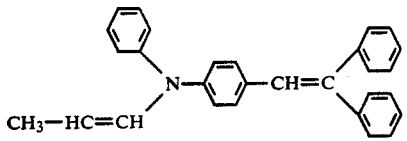
I-(6)

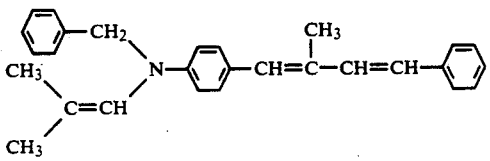
I-(7)

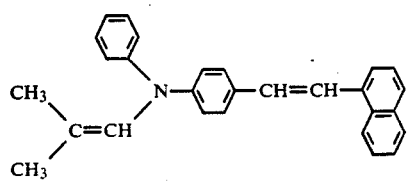
I-(8)

-continued
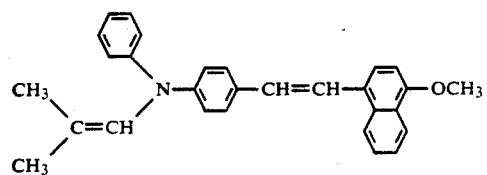 I-(9)
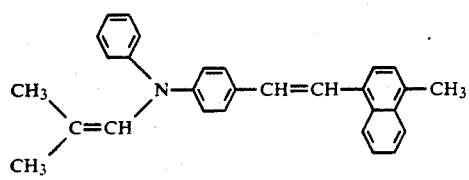 I-(10)
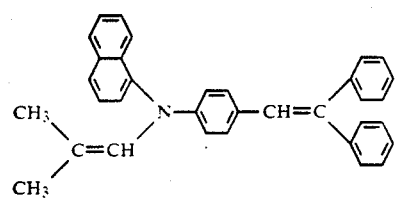 I-(11)
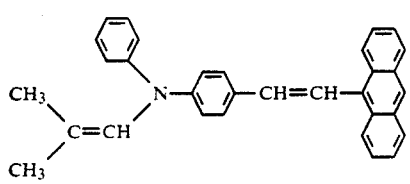 I-(12)
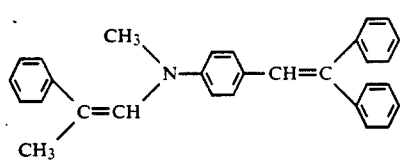 I-(13)
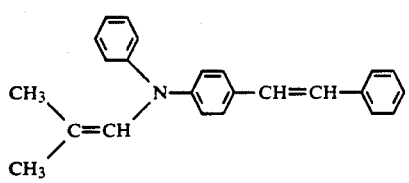 I-(14)
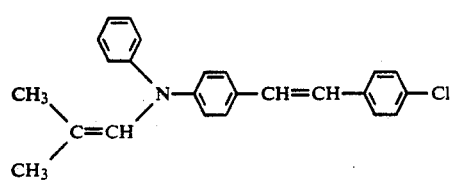 I-(15)
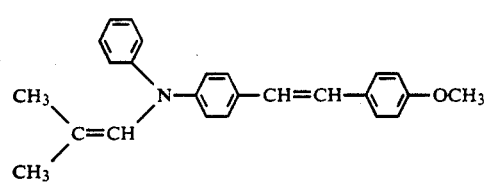 I-(16)
-continued
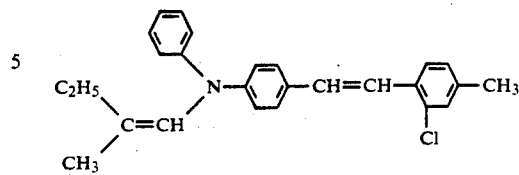 I-(17)
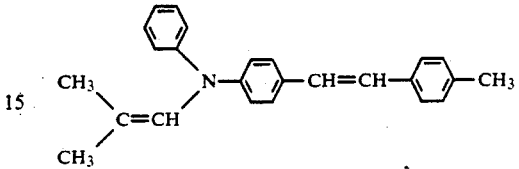 I-(18)
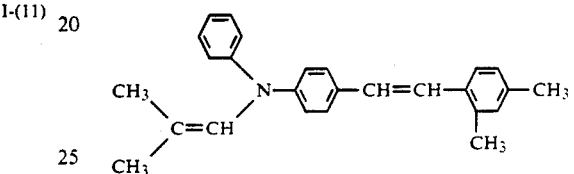 I-(19)
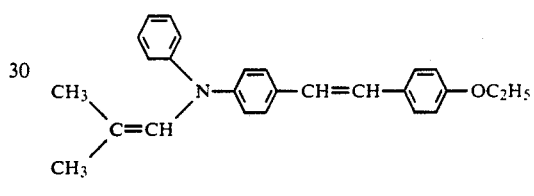 I-(20)
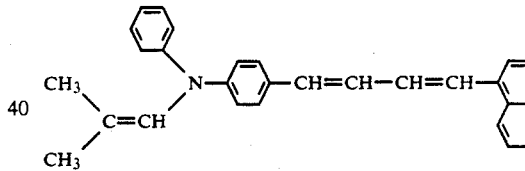 I-(21)
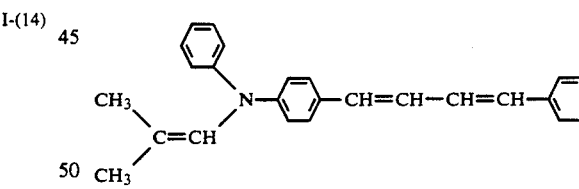 I-(22)
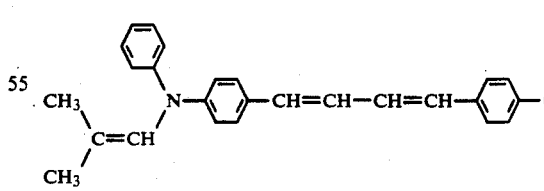 I-(23)
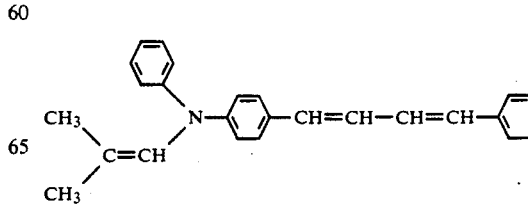 I-(24)

I-(25)
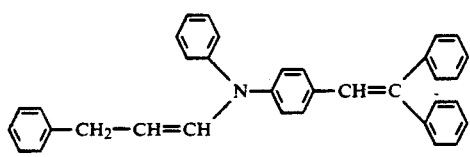
Examples of the compound represented by the formula [II]
II-(1)
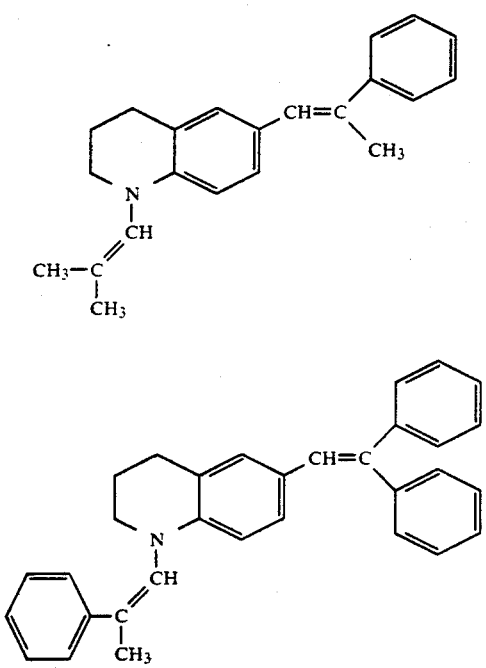
II-(5)
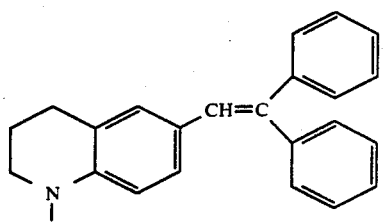
II-(6)
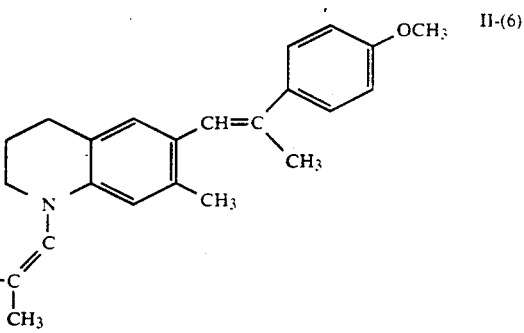
II-(3)
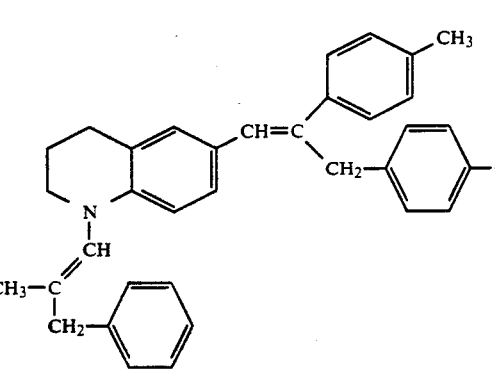
II-(7)
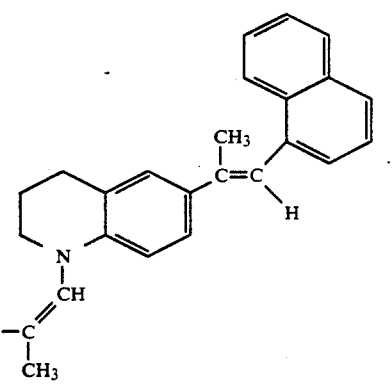
II-(4)
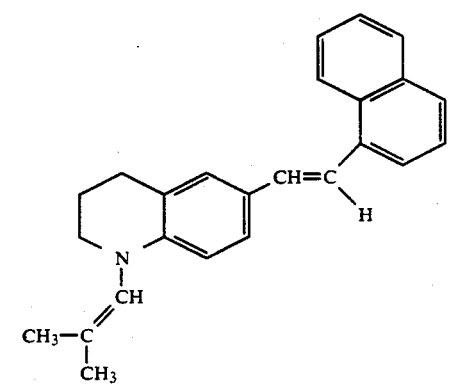
II-(8)
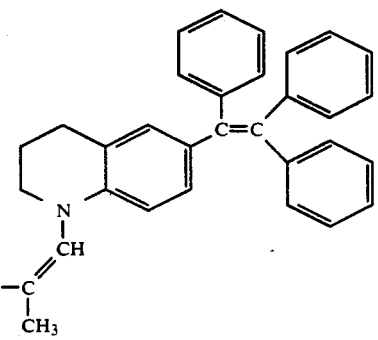

-continued
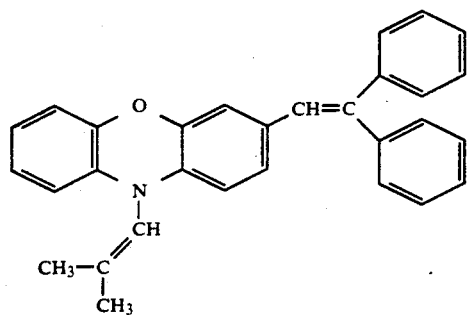
II-(9)
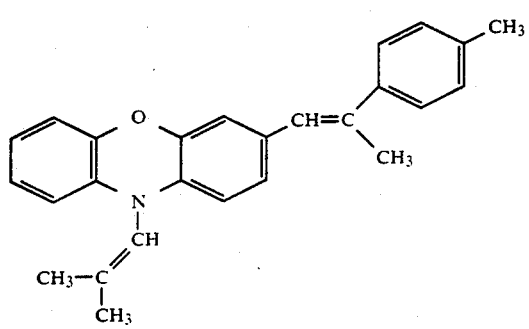
II(10)
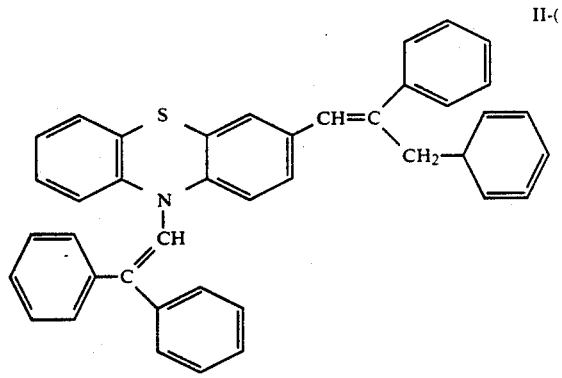
II-(11)
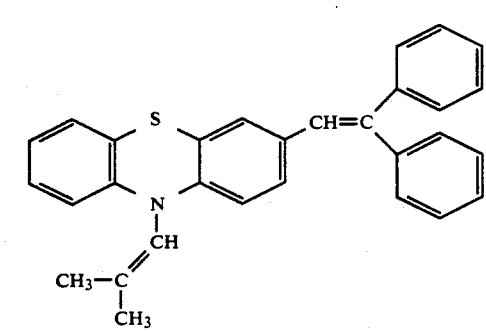
II-(12)
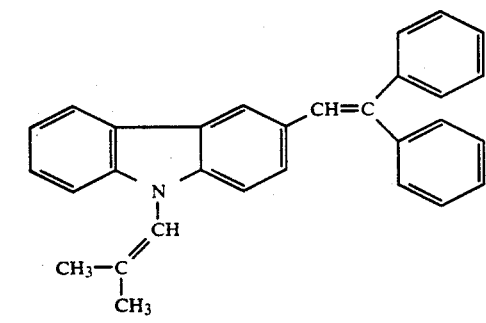
II-(13)
-continued
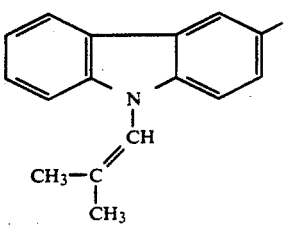
II-(14)
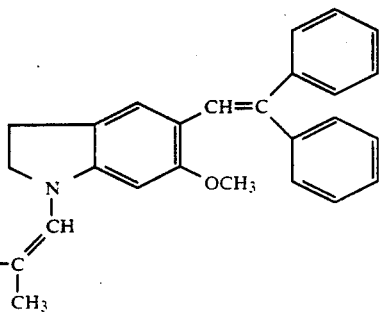
II-(15)
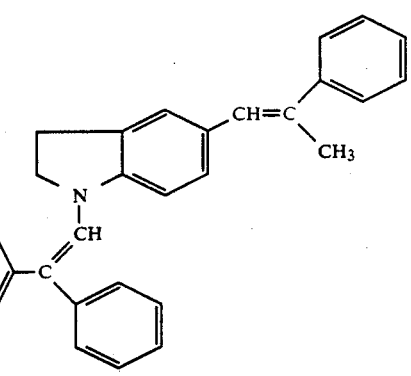
II-(16)
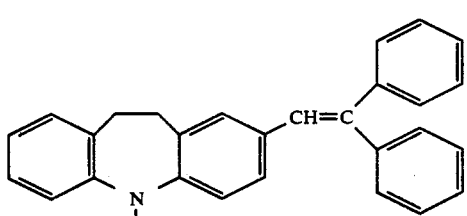
II(17)
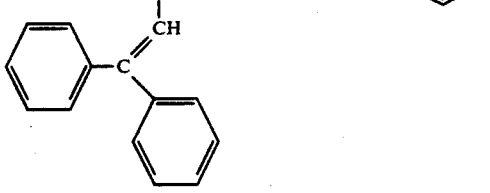
Example of the compound represented by the formula [III]

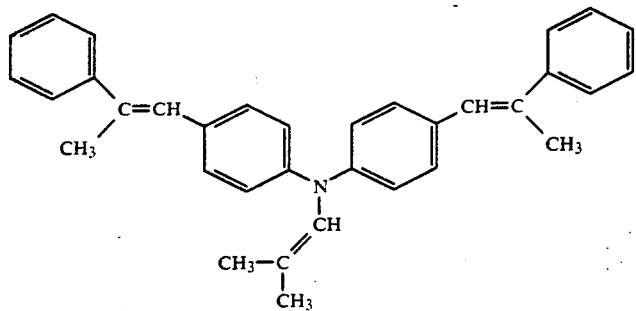
III-(1)
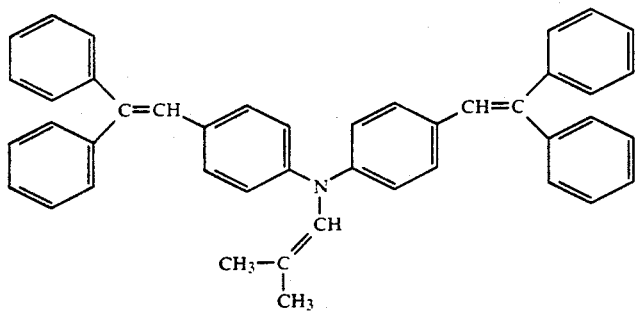
III-(2)
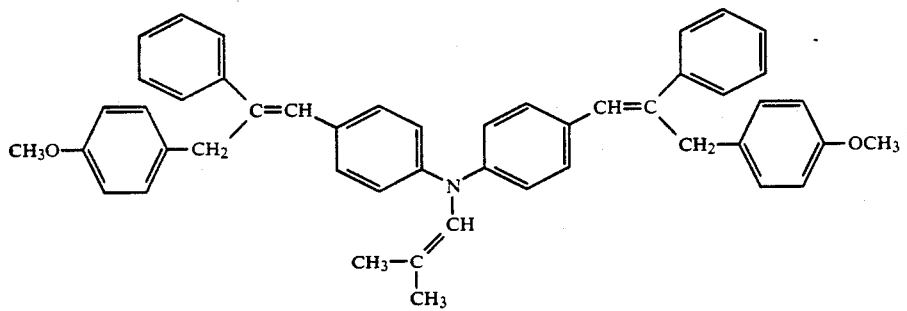
III-(3)
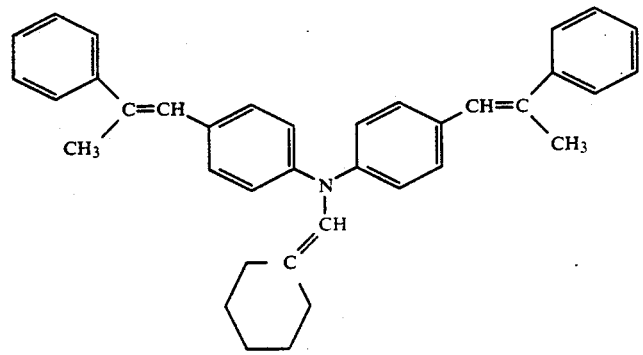
III-(4)

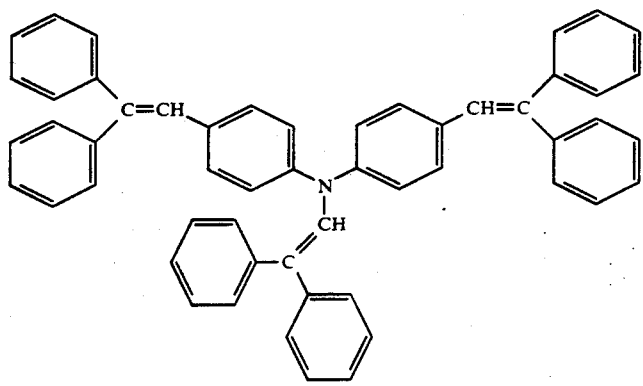
III-(5)
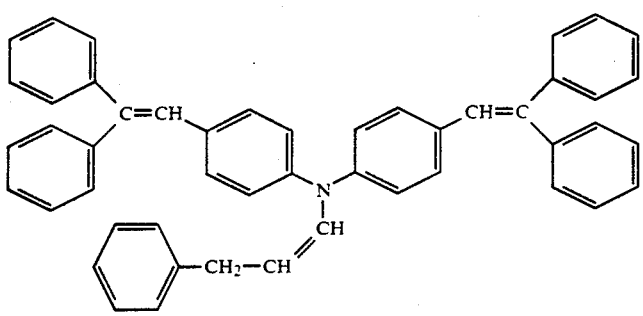
III-(6)
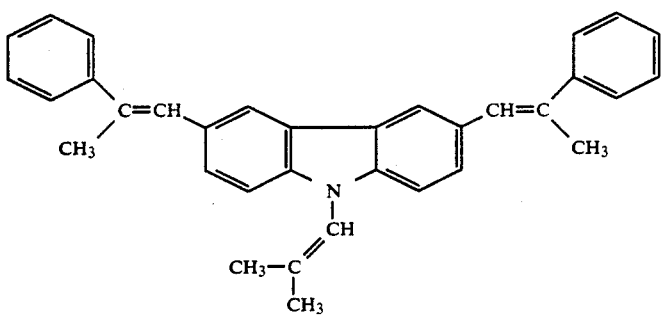
III-(7)
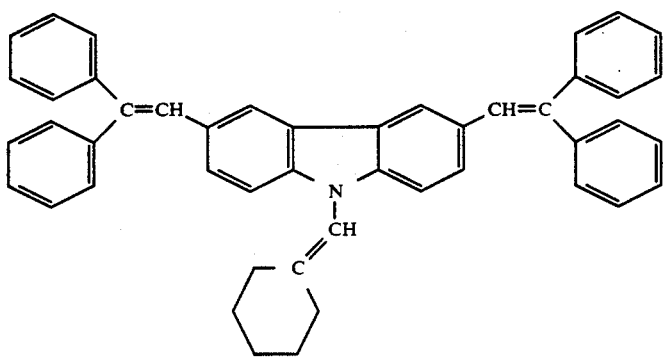
III-(8)

-continued
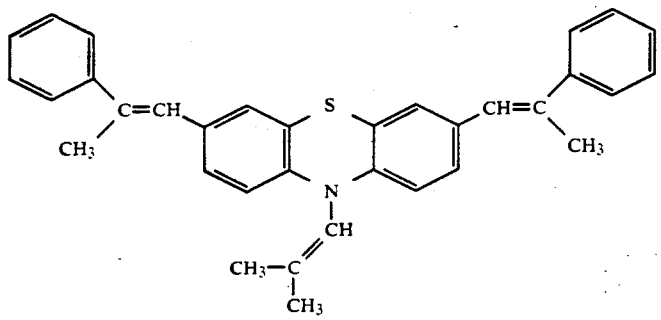
III-(9)
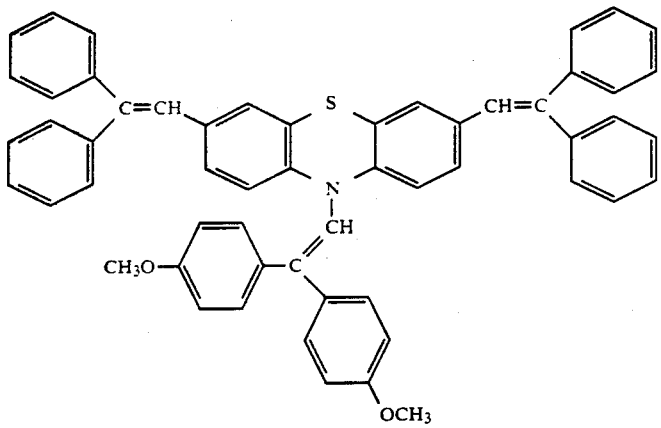
III-(10)
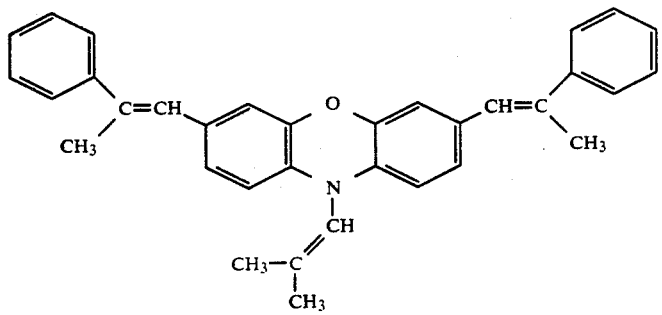
III-(11)
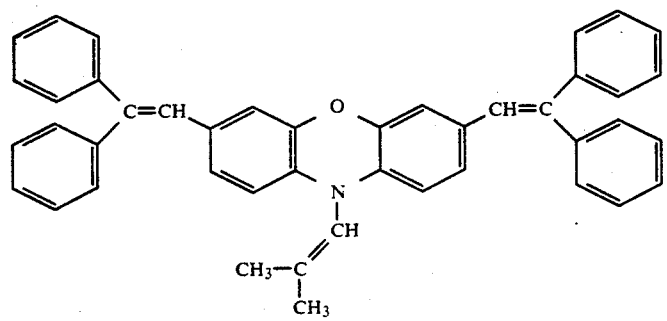
III-(12)

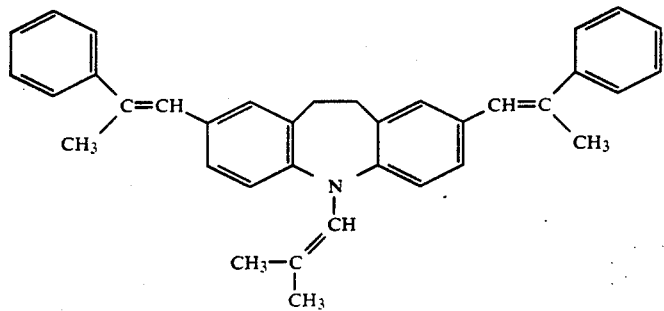
III-(13)
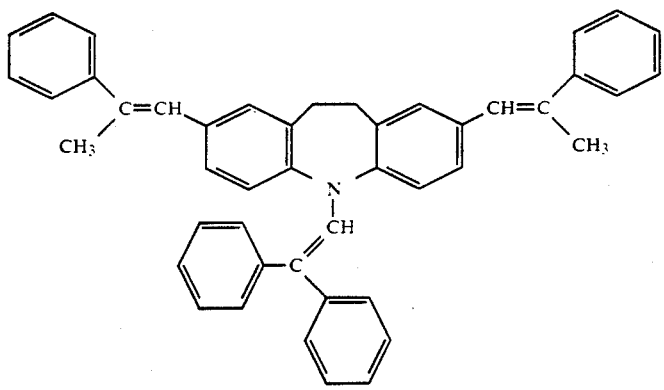
III-(14)
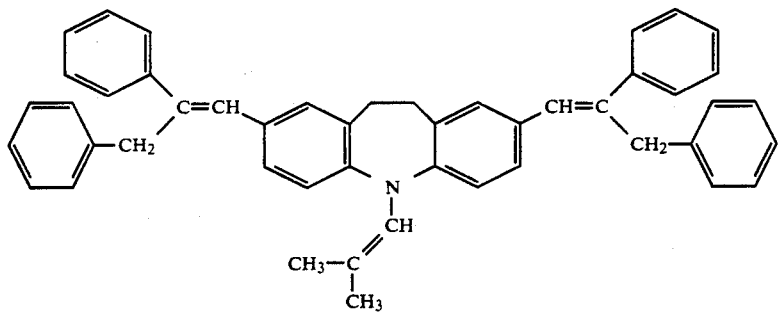
III-(15)
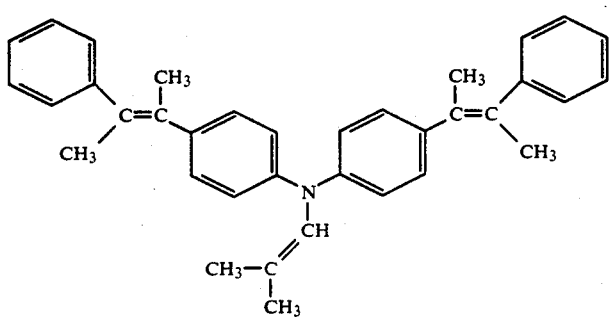
III-(16)

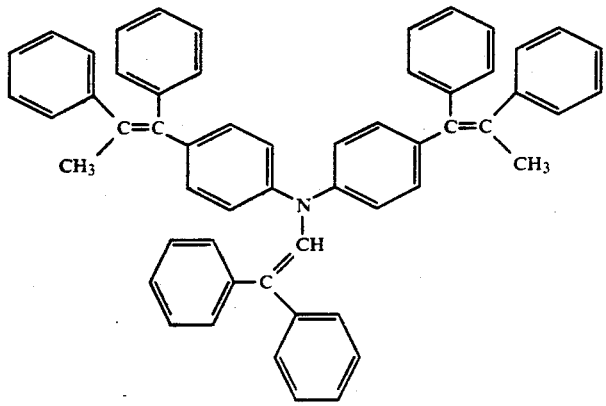

III-(17)

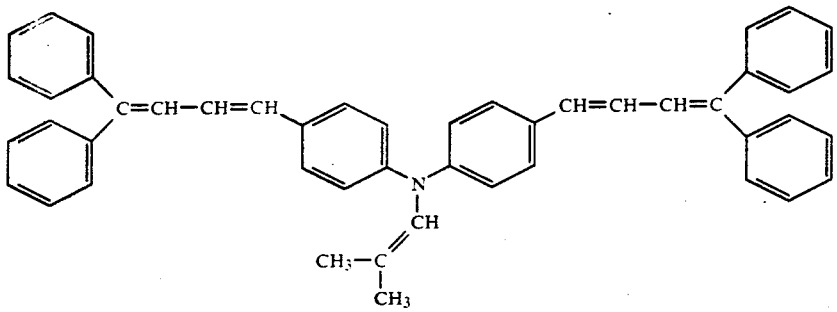

III-(18)

The electrophotographic photoreceptor of the present invention is obtained by containing one or more of the stilbene compounds as shown above and it has excellent properties.

Various methods have been known for use of these stilbene compounds as electrophotographic photoreceptor.

For example, there are a photoreceptor which comprises a conductive support on which is coated a solution or dispersion of the stilbene compound and a sensitizing dye in a binder resin, if necessary, with addition of a chemical sensitizer or an electron attractive compound; a photoreceptor in the form of a double layer structure comprising a carrier generation layer and a carrier transport layer wherein a carrier generation layer mainly composed of a carrier generation substance of high carrier generation efficiency such as dye or pigment is provided on a conductive support and thereon is provided a carrier transport layer comprising a solution or a dispersion of the stilbene compound in a binder resin, if necessary, with addition of a chemical sensitizer or an electron attractive compound; and such photoreceptor as mentioned above wherein the carrier generation layer and the carrier transport layer are provided in the reverse order. The stilbene compound of the present invention can be applied to all of these photoreceptors.

Support used for preparation of the photoreceptor using the stilbene compound according to the present invention includes, for example, a metallic drum, a metallic plate, or a sheet-like, drum-like or belt-like paper and plastic film subjected to electroconductive treatment.

As film-forming binder resins used for formation of photosensitive layer on the support, mentioned may be made of various resins depending on fields in which the photoreceptor is utilized. For example, in case of photoreceptors for copying, mention may be made of polystyrene resin, polyvinylacetal resin, polysulfone resin, polycarbonate resin, vinyl acetate/crotonic acid copolymer resin, polyphenylene oxide resin, polyester resin, alkyd resin, polyarylate resin, acrylic resin, methacrylic resin, and phenoxy resin. Among them, polystyrene resin, polyvinylacetal resin, polycarbonate resin, polyester resin, polyarylate resin, and phenol resin are superior in potential characteristics as photoreceptor.

These resins may be used singly or in combination as homopolymers or copolymers.

In case of using the photoreceptor as printing plate, alkali soluble binders are necessary. That is, preferred are resins having acidic group soluble in water or alcoholic alkaline solvents such as acid anhydride group, carboxyl group, phenolic hydroxyl group, sulfonic acid group, sulfonamide group or sulfoimide group and normally have an acid value of 100 or more. Examples of resins having high acid value suitable for these uses are copolymer resins such as styrene/maleic anhydride, vinyl acetate/maleic anhydride, vinyl acetate/crotonic acid, methacrylic acid/methacrylate ester, and methacrylic acid/styrene/methacrylate ester, and phenol resin.

Amount of these binder resins to be added to photoconductive compound is 2.0-10, preferably 0.5-5 times the weight of the photoconductive compound. If the amount is less than this range, the photoconductive compound is precipitated in or on the photosensitive layer to cause deterioration of adhesion to the support and if it is more than the range, sensitivity is reduced.

Further, some of the film-forming binder resins are rigid and low in mechanical strengths such as tensile strength, flexural strength and compression strength and in order to improve these properties, plasticity imparting materials can be added.

These materials include, for example, phthalate ester (such as DOP, DBP and DIDP), phasphate ester (such as TCP and TOP), sebacate ester, adipate ester, nitrile rubber, and chlorinated hydrocarbon. If these materials which impart plasticity are added in an amount more than needed, potential characteristics are deteriorated and so they are added preferably in an amount of 20% by weight or less of binder resin.

The sensitizing dyes added to the photosensitive layer include triphenylmethane dyes represented by Methyl Violet, Crystal Violet, Ethyl Violet, Night Blue, and Victoria Blue, xanthene dyes represented by erythrosine, Rhodamine B, Rhodamine 3B, and Acridine Red B, acridine dyes represented by Acridine Orange 2G, Acridine Orange R and Flaveosine, thiazine dyes represented by Methylene Blue and Methylene Green, oxazine dyes represented by Gapri Blue and Meldola's Blue, and other cyanine dyes, styryl dyes, pyrylium salts, thiapyrylium salts and squarylium salt dyes.

As photoconductive pigments which generate carrier at very high efficiency upon absorption of light, mention may be made of phthalocyanine pigments such as metal-free phthalocyanine and phthalocyanine containing various metals or metal compounds, perylene pigments such as peryleneimide and perylenic anhydride, and quinacridone pigments, anthraquinone pigments, and azo pigments.

Among these pigments, bisazo pigments, trisazo pigments and phthalocyanine pigments high in carrier generating efficiency afford high sensitivity and thus provide excellent electrophotographic photoreceptor.

The dye added to photosensitive layer can be used singly as a carrier generation substance, but joint use of this dye with pigment can generate carrier at higher efficiency. Furthermore, inorganic photoconductive substances include selenium, selenium-tellurium alloy, cadmium sulfide, zinc sulfide and amorphous silicon.

In addition to the above-mentioned sensitizers (so-called spectral sensitizers), there may be added sensitizers for further increase of sensitivity (so-called chemical sensitizers).

Such sensitizers include, for example, p-chlorophenol, m-chlorophenol, p-nitrophenol, 4-chloro-m-cresol, g-chlorobenzoylacetanilide, N,N'-diethylbarbituric acid, 3-(β-oxyethyl)-2-phenylimino-thiazolidone, malonic acid dianilide, 3,5,3',5'-tetrachloromalonic acid dianilide, α-naphthol, and p-nitrobenzoic acid.

Furthermore, it is also possible to add some electron attractive compounds as sensitizers which form a charge transport complex with the stilbene compound of the present invention to further enhance the sensitizing effect.

As the electron attractive substances, mention may be made of, for example, 1-chloroanthraquinone, 1-nitroanthraquinone, 2,3-dichloronaphthoquinone, 3,3-dinitrobenzophenone, 4-nitrobenzalmalononitrile, phthalic anhydride, 3-(α-cyano-p-nitrobenzal)phthalide, 2,4,7-trinitrofluorenone, 1-methyl-4-nitrofluorenone, and 2,7-dinitro-3,6-dimethylfluorenone.

If necessary, antioxidant, curl inhibitor, etc. may also be added to the photoreceptor.

The stilbene compound of the present invention is dissolved or dispersed in a suitable solvent together with the above-mentioned additives depending on the form of photoreceptor, the resulting coating liquid is coated on an electroconductive support mentioned above and is dried to obtain a photoreceptor.

As the coating solvent, for example, halogenated hydrocarbons such as chloroform, dichloroethane, trichlorethane, and trichloroethylene, aromatic hydrocarbons such as benzene, toluene, xylene, and monochlorobenzene, dioxane, tetrahydrofuran, and methylcellosolve acetate are used singly or as mixed solvent of two or more of them. If necessary, solvents such as alcohols, acetonitrile, N,N-dimethylformamide, and methyl ethyl ketone may further added to the above solvents.

The following nonlimiting examples further explain the present invention.

EXAMPLE 1

A solution prepared by dissolving bisazo pigment represented by the following formula in n-butylamine at a concentration of 1% by weight was coated on a polyester film clad with an aluminum foil (ALPET 85 manufactured by Mitsubishi Resin Co., Ltd.; film thickness: 85μ, aluminum foil thickness: 10μ) as a support and was dried to form a film of carrier generation material of 0.5μ thick.

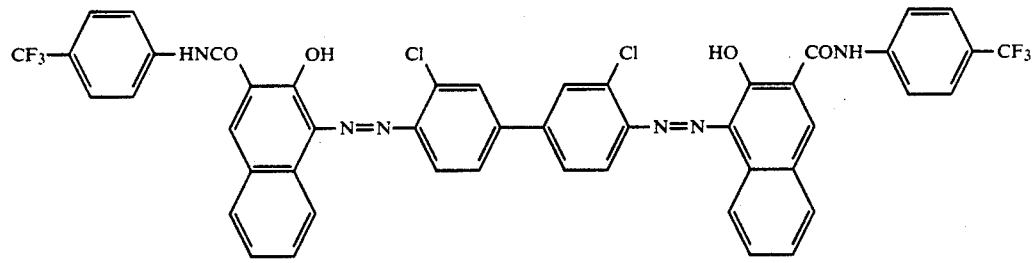

Then the stilbene compound of compound No. 1-(1) exemplified hereinbefore was mixed with a polyarylate resin (U-POLYMER manufactured by Unitrika Ltd.) at a weight ratio of 1:1 and the mixture was dissolved in dichloroethane as a solvent to prepare a 10% solution. This solution was coated on the film of the carrier generation material formed hereabove by an applicator to form a carrier transport layer having a dry thickness of 20μ.

Electrophotographic characteristics of the resulting double layer type electrophotographic photoreceptor were evaluated by an electrostatic recording paper testing apparatus (SP-428 manufactured by Kawaguchi Denki Seisakusho Co.).

Measuring conditions: Applied voltage −6 KV, Static No. 3.

As a result, half decay exposure with white light was 2.5 lux·sec which means very high sensitivity. In addition, evaluation of repetition characteristics was conducted using this apparatus. As a result of repeated use of $10^3$ times, initial potential at the first time was −1050

V and that at $10^3$th time was $-1030$ V. Thus, it can be seen that it was stable.

EXAMPLES 2-6

Photoreceptors were prepared in the same manner as in Example 1 except that stilbene compounds shown in Table 1 were used in place of the stilbene compound used in Example 1. Half decay exposure E1/2 (lux·sec) and initial potential $V_o$ (volt) of the resulting photoreceptors were measured under the same measuring conditions as in Example 1 and the results are shown in Table 1. Further, one test cycle of charging-removing of potential (light for removal of potential: white light of 400 lux × 1 second) was repeated $10^3$ times and initial potential $V_o$ (volt) and half decay exposure E1/2 are shown in Table 1.

TABLE 1

| | | The 1st cycle | | The $10^3$th cycle | |
|---|---|---|---|---|---|
| Example | Compound | $V_o$ (volt) | E½ (lux·sec) | $V_o$ (volt) | E½ (lux·sec) |
| 2 | I-(2) | −980 | 2.6 | −960 | 2.5 |
| 3 | I-(6) | −930 | 3.8 | −900 | 3.7 |
| 4 | I-(8) | −870 | 2.3 | −830 | 2.0 |
| 5 | I-(10) | −880 | 2.7 | −860 | 2.4 |
| 6 | I-(12) | −1010 | 3.1 | −990 | 3.1 |

EXAMPLE 7

A bisazo pigment having the following formula was used in place of the pigment used in Example 1.

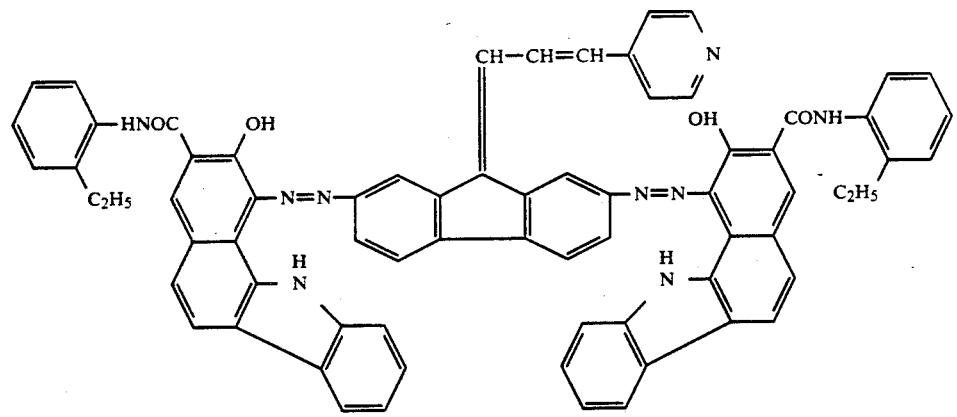

That is, 1 part by weight of this pigment and 1 part by weight of a polyester resin (BYRON 200 manufactured by Toyobo Co., Ltd.) were mixed with 100 parts by weight of tetrahydrofuran and the mixture was dispersed by a paint conditioner apparatus together with glass beads for 2 hours. The resulting pigment dispersion was coated on the same support as used in Example 1 by an applicator to form a carrier generation layer. Thickness of this thin film was about 0.2μ.

Then, a carrier transport layer was formed in the same manner as in Example 1 using compound I-(8) exemplified herebefore to obtain a photoreceptor. This photoreceptor was evaluated under the same measuring conditions as in Example 1. $V_o$ was −810 volt and E1/2 was 1.8 lux·sec.

EXAMPLES 8-12

Photoreceptors were prepared in the same manner as in Example 7 except that stilbene compounds shown in Table 2 were used and were evaluated under the same measuring conditions as in Example 1. The results are shown in Table 2.

TABLE 2

| | | The 1st cycle | | The $10^3$th cycle | |
|---|---|---|---|---|---|
| Example | Compound | $V_o$ (volt) | E½ (lux·sec) | $V_o$ (volt) | E½ (lux·sec) |
| 8 | I-(1) | −790 | 1.7 | −780 | 1.7 |
| 9 | I-(6) | −820 | 1.9 | −810 | 1.8 |
| 10 | I-(12) | −760 | 1.6 | −760 | 1.4 |
| 11 | I-(15) | −740 | 1.9 | −710 | 1.7 |
| 12 | I-(24) | −760 | 2.0 | −750 | 1.9 |

EXAMPLE 13

Styrene/n-butyl methacrylate/methacrylic acid copolymer (acid value 185) and compound I-(1) were mixed at a weight ratio of 1.5:1 and thereto was added ε-copper phthalocyanine in an amount of 10% by weight of the stilbene compound and the mixture was dispersed in a ball mill with addition of dioxane solvent so that total solid content was 30% by weight. This dispersion was coated on an aluminum plate which had been sandblasted and surface oxidized by a wire bar and dried to obtain a photoreceptor for printing plate which has a film thickness of about 4μ.

This photoreceptor was evaluated on electrophotographic characteristics by the above electrostatic recording paper testing apparatus. Measurement was conducted under the evaluation conditions: Applied voltage −5.5 KV, Static No. 3 to obtain an initial potential of −410 volts and a half decay exposure of 7.5 lux·sec.

This photoreceptor was subjected to toner development and then to etching treatment with an alkali processing solution (for example, an aqueous solution containing 3% of triethanolamine, 10% of ammonium carbonate and 20% of polyethylene glycol having a mean molecular weight of 190-210). Non-image portions were easily dissolved out and toner images remained. Then, the surface of this plate was treated with water containing sodium silicate to obtain a strong printing plate.

It was found that printing endurance of this printing plate in offset printing was more than 50,000 prints.

EXAMPLE 14

One part by weight of a pigment represented by the following formula and 1 part by weight of a polyester resin (BYRON 200 manufactured by Toyobo Co., Ltd.) were mixed with 100 parts by weight of tetrahydrofuran and the mixture was dispersed together with glass beads for 2 hours by a paint conditioner apparatus.

charging and removing of potential (by exposing to white light of 400 lux for 1 second) and initial potential

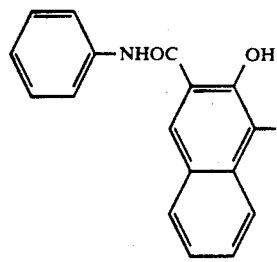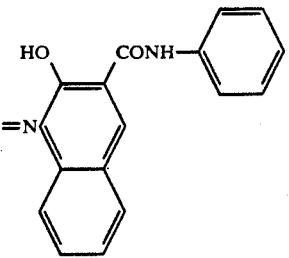

The resulting pigment dispersion was coated on an aluminum vapor deposited polyester film by an applicator to form a film of carrier generation substance of about 0.2μ thick.

Then, stilbene compound II-(1) and a polyarylate resin (U-POLYMER manufactured by Unitika Ltd.) were mixed at a weight ratio of 1:1 and 10% solution of this mixture in dichloroethane as a solvent was prepared. This solution was coated on the film of the carrier generation substance by an applicator to form a carrier transport layer of 20μ in dry thickness.

Thus obtained electrophotographic photoreceptor was evaluated on its electrophotographic characteristics by the same electrostatic recording paper testing apparatus as used in Example 1 under the measuring conditions of applied voltage −6 KV, static No. 3.

The half decay exposure for white light was 2.8 lux·sec which indicates very high sensitivity.

Evaluation for repeated use was conducted using the above apparatus. Change in potential by repetition of $10^3$ times was examined to obtain initial potential of −1000 V for the first time and initial potential at $10^3$th time of −960 V. It can be seen that reduction of potential due to repetition was small and potential was stable. Thus, excellent characteristics were exhibited.

EXAMPLES 15-18

Photoreceptors were prepared in the same manner as in Example 14 except that stilbene compounds shown in Table 3 were used in place of the compound used in Example 14. Half decay exposure E1/2 (lux·sec) and initial potential $V_o$ (volt) were measured under the same measuring conditions as in Example 14 and the results are shown in Table 3. Furthermore, the photoreceptors were subjected to $10^3$ test cycles, each cycle comprising $V_o$ (volt) and half decay exposure are shown in Table 3.

TABLE 3

| | | The 1st cycle | | The 1000th cycle | |
|---|---|---|---|---|---|
| Example | Compound | $V_o$ (volt) | $E_{\frac{1}{2}}$ (lux·sec) | $V_o$ (volt) | $E_{\frac{1}{2}}$ (lux·sec) |
| 15 | II-(4) | −1010 | 2.8 | −980 | 2.8 |
| 16 | II-(12) | −980 | 2.5 | −940 | 2.4 |
| 17 | II-(13) | −950 | 2.7 | −940 | 2.7 |
| 18 | II-(16) | −990 | 3.0 | −930 | 2.8 |

EXAMPLES 19-22

A bisazo pigment having the following formula was used as charge generation substance.

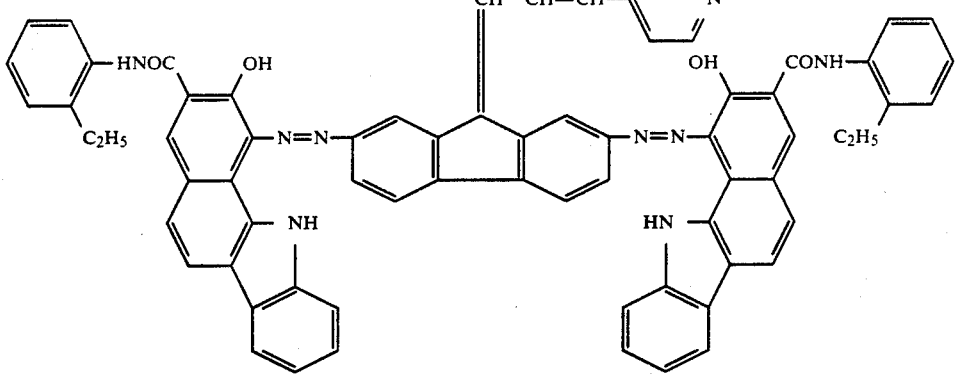

That is, 1 part by weight of this pigment and 1 part by weight of a polyester resin (BYRON 200) were mixed with 100 parts by weight of tetrahydrofuran and the mixture was dispersed together with glass beads for 2 hours by a paint conditioner apparatus. The resulting pigment dispersion was coated on the same support as used in Example 14 by an applicator to form a carrier generation layer. Thickness of this layer was about 0.2μ.

Thereafter, carrier transport layer was formed thereon using the compounds as shown in Table 4 in the same manner as in Example 14 to make photoreceptors. The resulting photoreceptors were evaluated in the same manner as in Example 14. The results are shown in Table 4.

TABLE 4

| | | The 1st cycle | | The 1000th cycle | |
|---|---|---|---|---|---|
| Example | Compound | $V_o$ (volt) | $E_{\frac{1}{2}}$ (lux·sec) | $V_o$ (volt) | $E_{\frac{1}{2}}$ (lux·sec) |
| 19 | II-(4) | −920 | 1.5 | −910 | 1.5 |
| 20 | II-(12) | −950 | 1.4 | −920 | 1.3 |
| 21 | II-(13) | −910 | 1.5 | −900 | 1.5 |
| 22 | II-(16) | −980 | 1.5 | −920 | 1.4 |

EXAMPLE 23

One part by weight of a pigment represented by the following formula and 1 part by weight of a polyester resin (BYRON 200) were mixed with 100 parts by weight of tetrahydrofuran and the mixture was dispersed together with glass beads for 2 hours by a paint conditioner apparatus.

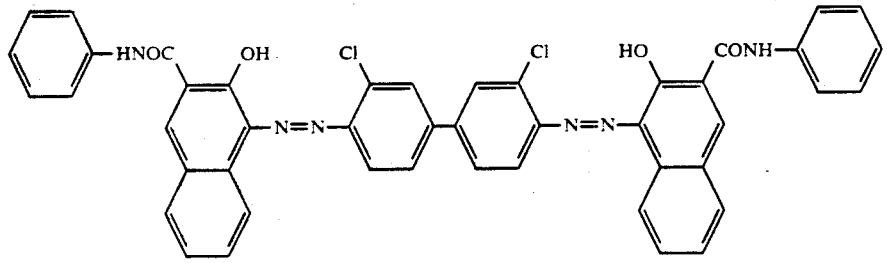

The resulting pigment dispersion was coated on an aluminum vapor deposited polyester film by an applicator and dried to form a film of carrier generation substance of about $0.2\mu$ thick.

Then, stilbene compound represented by III-(1) was mixed with a polyarylate resin (U-POLYMER manufacture by Unitika Ltd.) at 1:1 and a 10% solution of the mixture in dichloroethane was prepared. This solution was coated on the film of carrier generation substance formed hereabove by an applicator to form a carrier transport layer of $20\mu$ in dry thickness.

The resulting laminate photoreceptor was evaluated in the same manner as in Example 14. Half decay exposure for white light was 2.4 lux·sec which means a very high sensitivity.

Furthermore, evaluation for repeated use was conducted. Change in potential due to repeated use of $10^3$ times was examined. Initial potential of the first time was −1020 V and initial potential of $10^3$th time was −1000 V. It can be seen that reduction in potential due to repeated use was small and the potential was stable. Thus, excellent characteristics were exhibited.

EXAMPLES 24-27

Photoreceptors were prepared in the same manner as in Example 23 except that stilbene compounds shown in Table 5 were used in place of the stilbene compound used in Example 23 and half decay exposure E1/2 (lux·sec) and initial potential $V_o$ (volt) were measured under the same measuring conditions as in Example 23. The results are shown in Table 5. Furthermore, these photoreceptors were subjected to $10^3$ test cycles, each cycle consisting of charging and removing of potential (removing of potential was carried out by exposing to white light of 400 lux for 1 sec) and initial potential $V_o$ (volt) and half decay exposure are shown in Table 5.

TABLLE 5

| | | The 1st cycle | | The 1000th cycle | |
|---|---|---|---|---|---|
| Example | Compound | $V_o$ (volt) | $E_{\frac{1}{2}}$ (lux·sec) | $V_o$ (volt) | $E_{\frac{1}{2}}$ (lux·sec) |
| 24 | III-(2) | −970 | 2.6 | −950 | 2.6 |
| 25 | III-(5) | −1010 | 2.8 | −980 | 2.7 |
| 26 | III-(7) | −910 | 2.8 | −900 | 2.8 |
| 27 | III-(17) | −980 | 3.1 | −950 | 3.0 |

EXAMPLES 28-31

A bisazo pigment of the following formula was used as carrier generation substance.

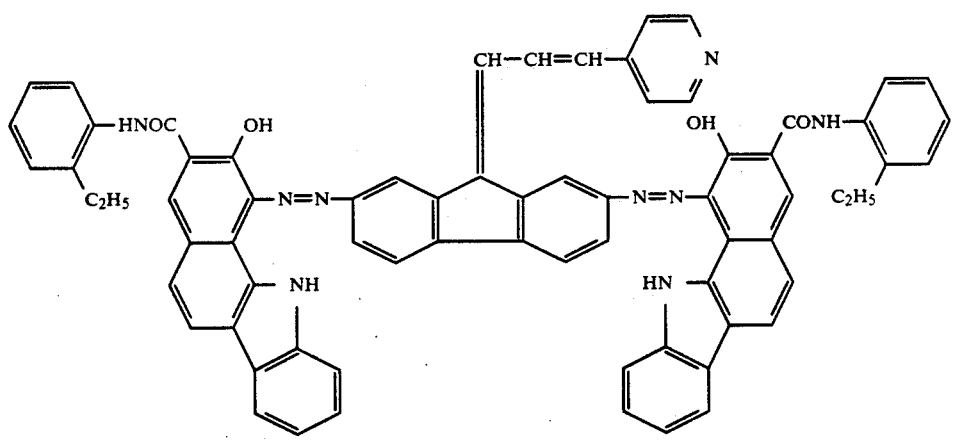

That is, 1 part by weight of this pigment and 1 part by weight of a polyester resin (BYRON 200) were mixed with 100 parts by weight of tetrahydrofuran and the mixture was dispersed together with glass beads for 2 hours by a paint conditioner apparatus. The resulting pigment dispersion was coated on the same support as used in Example 23 by an applicator to form a carrier generation layer of about 0.2μ. thick.

Then, carrier transport layer was formed in the same manner as in Example 23 using compounds shown in Table 6 to make photoreceptors. These photoreceptors were evaluated under the same measuring conditions as in Example 23. The results are shown in Table 6.

TABLE 6

| | | The 1st cycle | | The 1000th cycle | |
|---|---|---|---|---|---|
| Example | Compound | $V_o$ (volt) | $E_{\frac{1}{2}}$ (lux·sec) | $V_o$ (volt) | $E_{\frac{1}{2}}$ (lux·sec) |
| 28 | III-(2) | −950 | 1.6 | −910 | 1.5 |
| 29 | III-(5) | −960 | 1.7 | −930 | 1.7 |
| 30 | III-(7) | −900 | 1.8 | −890 | 1.8 |
| 31 | III-(9) | −850 | 2.0 | −800 | 1.9 |

What is claimed is:

1. An electrophotographic photoreceptor which comprises an electroconductive support and, provided thereon, a photosensitive layer which contains a stilbene compound represented by the following formula [I], [II], or [III]:

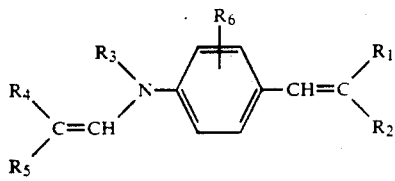

wherein $R_1$ and $R_2$ which may be identical or different each is a hydrogen atom or an alkyl, aryl, or styryl group which may have substituent and at least one of them is an aryl or styryl group which may have substituent; $R_3$ is an alkyl, aralkyl or aryl group which may have substituent; $R_4$ and $R_5$ which may be identical or different each is a hydrogen atom, or an alkyl, benzyl or phenyl group which may have substituent, and $R_6$ is a hydrogen atom, or an alkyl or alkoxy group which may have substituent, or a halogen atom;

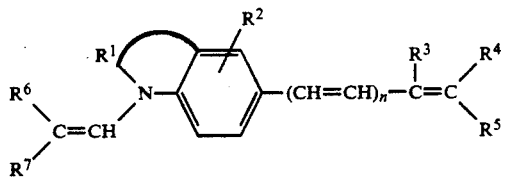

wherein $R^1$ is an atom group necessary to form a ring together with nitrogen atom; $R^2$ is a hydrogen atom, or an alkyl or alkoxy group which may have substituent; $R^3$ is a hydrogen atom, or an alkyl or aryl group which may have substituent; $R^4$ is an aryl group which may have substituent; $R^5$ is a hydrogen atom, or an alkyl, aralkyl or aryl group which may have substituent; $R^6$ and $R^7$ which may be identical of different each is a hydrogen atom, or an alkyl, aralkyl or aryl group which may have substituent and $R^6$ and $R^7$ may form a ring; and n is 0 or 1; or

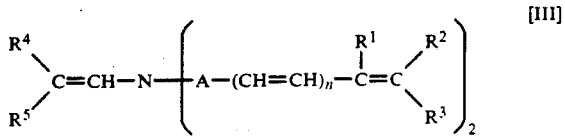

wherein A is an aromatic ring and the two A may link through a bond, an atom or an atom group to form a heterocyclic ring together with nitrogen atom; $R^1$ is a hydrogen atom, or an alkyl or aryl group which may have substituent; $R^2$ is an aryl group which may have substituent; $R^3$ is an alkyl, aralkyl or aryl group which may have substituent; $R^4$ and $R^5$ which may be identical or different each is a hydrogen atom, or an alkyl, aralkyl or aryl group which may have substituent and $R^4$ and $R^5$ may form a ring; and n is 0 or 1.

2. An electrophotographic photoreceptor according to claim 1, wherein the photosensitive layer contains the stilbene compound dissolved or dispersed in a binder resin.

3. An electrophotographic photoreceptor according to claim 1, wherein the photosensitive layer contains the stilbene compound and a carrier generation material.

4. An electrophotographic photoreceptor according to claim 1, wherein the photosensitive layer comprises a carrier generation layer and a carrier transport layer which contains the stilbene compound.

5. An electrophotographic photoreceptor according to claim 4, which comprises an electroconductive support, a carrier generation layer provided on the support and a carrier transport layer provided on the carrier generation layer.

6. An electrophotographic photoreceptor according to claim 2, wherein amount of the binder resin is 0.2–10 times the weight of the stilbene compound.

7. An electrophotographic photoreceptor according to claim 2, wherein amount of the binder resin is 0.5–5 times the weight of the stilbene compound.

8. An electrophotographic photoreceptor according to claim 1, wherein the electroconductive support is a metallic drum, a metallic plate, or a sheet-like drum-like or belt-like paper or plastic film subjected to electroconductive treatment.

9. An electrophotographic photoreceptor according to claim 2, which is a lithographic printing plate and wherein the binder resin is an alkali soluble resin.

* * * * *